United States Patent
Busch et al.

(10) Patent No.: US 7,536,827 B2
(45) Date of Patent: May 26, 2009

(54) HYDROPONIC GROWING ENCLOSURE AND METHOD FOR GROWING, HARVESTING, PROCESSING AND DISTRIBUTING ALGAE, RELATED MICROORGANISMS AND THEIR BY PRODUCTS

(75) Inventors: Gail Busch, Montpelier, VT (US); Jacques M. Dupont, Alton, IL (US)

(73) Assignee: Algepower LLC, St. Louis, MO (US)

( * ) Notice: Subject to any disclaimer, the term of this patent is extended or adjusted under 35 U.S.C. 154(b) by 0 days.

(21) Appl. No.: 11/840,533

(22) Filed: Aug. 17, 2007

(65) Prior Publication Data

US 2008/0052987 A1 Mar. 6, 2008

Related U.S. Application Data

(60) Provisional application No. 60/822,667, filed on Aug. 17, 2006.

(51) Int. Cl.
*A01G 31/00* (2006.01)
*A01G 31/06* (2006.01)
*C12P 5/00* (2006.01)

(52) U.S. Cl. .............................. 47/62 R; 47/1.4; 47/39; 47/59 R; 435/134; 435/166; 435/167; 435/257.1; 435/292.1; 435/420; 209/4; 209/5

(58) Field of Classification Search ...................... None
See application file for complete search history.

(56) References Cited

U.S. PATENT DOCUMENTS

| 6,579,714 | B1 * | 6/2003 | Hirabayashi et al. ..... 435/292.1 |
| 7,176,024 | B2 * | 2/2007 | Branson et al. .......... 435/292.1 |
| 2005/0239182 | A1 * | 10/2005 | Berzin ........................ 435/166 |

FOREIGN PATENT DOCUMENTS

WO 2007/025145 A2 3/2007

OTHER PUBLICATIONS

Jones, W.D., "The Power of Pond Scum: Biodiesel and Hydrogen From Algae," IEEE Spectrum, http://www.spectrum.ieee.org/print/6175, Apr. 21, 2008.

* cited by examiner

*Primary Examiner*—Herbert J. Lilling
(74) *Attorney, Agent, or Firm*—Lewis, Rice & Fingersh, L.C.

(57) ABSTRACT

Systems and methods for hydroponically growing microorganisms within a self-contained air-supported structure, in which microorganisms are grown in an organic slurry, harvested, and processed to obtain and process and distribute molecules useful for biofuel or other purposes.

42 Claims, 14 Drawing Sheets

HYDROPONIC GROWING ENCLOSURE AND METHOD FOR GROWING, HARVESTING, PROCESSING AND DISTRIBUTING ALGAE, RELATED MICROORGANISMS AND THEIR BY PRODUCTS

CROSS REFERENCE TO RELATED APPLICATION(S)

This application claims benefit of U.S. Provisional Patent Application Ser. No. 60/822,667 filed Aug. 17, 2006, the entire disclosure of which is herein incorporated by reference.

BACKGROUND

1. Field of the Invention

The present invention relates to a hydroponic growing system and a method of growing, harvesting, processing and distributing algae or other microorganisms And their benefits, uses and by-products, including, but not limited to bio diesel, animal feed, fertilizer, pharmaceuticals and the like.

2. Description of the Related Art

Photosynthetic organisms, or more commonly plants, can produce virtually any substance man has need of. For many years plants have produced foodstuffs, clothing materials, and other basics necessary for the survival of humankind. Recently, bioengineered plants have been developed that produce other useful materials such as designed pharmaceuticals and chemical intermediates. Further, even the most basic of plants can be used to help remove carbon dioxide from the Earth's air. This is an important benefit as increased levels of carbon dioxide from an industrial society are linked to global warming and environmental detriment.

One use of plants which has recently been of renewed interest is their provision of clean energy. While plant matter has been burned for fuel since the early history of mankind, recently the use of plants as a source for variable combustable materials which can be used for motor fuel has seen increased interest. Nations around the world are beginning to recognize that emissions from motor fuels, particularly gasoline and diesel fuel, are undesirable. Further, current materials which are generally petrochemicals refined from geologic deposits, are a limited resource and fuels which can potentially supersede them are of particular scientific interest. The burning of many plant based products is cleaner than the burning of petroleum products, resulting in improved environmental conditions; and is a renewable source of fuel.

Currently the two most well known bio-fuels which are seeing a large amount of press are ethanol, an alcohol generally made from sugarcane, rapeseed, corn, or other plant matter which is used as an additive to gasoline; and biodiesel, which is a mixture of diesel fuel with various forms of plant oil (generally soybean or rapeseed oil). Biodiesel may also comprise pure vegetable oils or vegetable oil blends, in some cases burning cooking oils. In the current world, both ethanol and plant oil based materials are used as additives to existing petrochemicals to provide for mixtures due to both price and consumer interest in these materials. Further, as current motor vehicles are not necessarily optimized for operation on these fuels, mixtures often produce better resultant fuel economy (where fuel is broadly defined to include the petrochemical and additive blend) than burning the additive alone.

Gasoline engines can also have trouble with the lighter ethanol material. In the future it is expected that engines will be built which are designed to run on these types of fuels exclusively and obtain better efficiency than today's engines which are not necessarily optimized for use with these types of fuels. Even today, however, desire to eliminate dependence on oil is making these types of products more and more economically sound. With the development of the carbon credit market, whereby environmentally friendly means of generating energy also generate credits with a monetary market value which can be sold to less environmentally friendly enterprises, advances from oil to biofuels may also be profitable.

While these fuels are already making a relatively significant change in the way that the human population thinks about motor fuel, both fuels have one significant shortfall. While the underlying source of the fuels can be grown in a regular cycle, both fuels are currently based on relatively complex plant forms (such as rapeseed, corn, and soybeans). While these crops are grown in huge numbers by agriculture around the world and are well understood, the plants still take a significant amount of time to grow which necessarily limits crop size. Further, the processes to turn these devices into fuel often only utilize the seed kernel or other product of the plant and are unable to utilize all the plant structure in fuel production. While the discarded components may be useful elsewhere, demand for fuel can lead to an excess of plant products not useful in its production.

While oils and alcohols to be used can be derived from virtually any type of plant, the current use of more complex life forms creates unnecessary waste and problems from fertilizer runoff and complicated markets. In particular, most foodstuffs, animal feeds, and raw materials formed by plants and used by humans are from relatively complex organisms. While much of the plant waste is used as animal feed or bedding, or may be left on the field as a form of fertilizer, this means that humans get very little value from a plant compared to the actual biomass of the plant produced.

This shortfall results in two significant concerns in the use of these materials as motor fuels. In the first instance, the supply of raw materials is cyclical over a relatively long period. Often only one or two harvests of the raw material can be made every year. This results in the need to plan ahead for demand needs. Further, because the plant growing cycle is necessarily dependent on the weather and various other related factors outside of the growers' control, the cyclical pattern is also somewhat unpredictable. In this way the cost of the fuels can become unexpected and can experience fluctuations which are undesirable to the eventual consumer.

Because of these types of problems, it is expected that, in the future, photosynthetic microorganisms such as algae, Cyanobacteria, plankton, and similar lifeforms will play a larger role than higher plants in photosynthetic carbon dioxide fixation because they have higher photosynthetic rates per unit biomass and, if optimized, can be cultivated in a compact space.

The potential of algae, Cyanobacteria, and other similar microorganisms as a food staple in the human diet has been investigated over many years in several countries. In the US and Japan, algal biomass including *Chlorella* and *Spirulina* is produced commercially, primarily as health food and is available for human consumption through a relatively large number of outlets. Algae are also used in lagoons on farms to process livestock waste and thereby lower amounts of pollutants, including phosphorus and nitrogen, in ground-water.

Further, algae and other microorganisms can be used as a raw material for the production of oil or alcohol to be used as a motor fuel. The high lipid content of many microalgae produces high natural omega-3 content which can be useful for human consumption or in the production of nutritional supplements as well as making it particularly valuable as a source of oil for motor fuel. It is also believed that algae can produce up to 60 percent of their weight in useful fuel molecules called triacylglycerols. It should be recognized that algae and other microorganisms can be used for a number of purposes and the system and methods discussed herein can be used for the production of these materials for any purpose.

Production of algae under current standards, however, would be expected to be unable to meet demand if algae products were used for motor fuel or otherwise became widespread. In particular, traditionally algae and Cyanobacteria have been grown only in laboratory photobioreactors which are not viable for commercial production, and in outdoor raceways, in open lakes, and in oceans. While these later methods are effective at producing algae for commercial use, these types of systems require vast amounts of space compared to the amount of algae they produce and are relatively difficult to harvest and keep clear of contamination. Further, just like other crops, photosynthetic microorganisms produced in outdoor raceways are at the mercy of the weather and contamination.

Hydroponics is the art of growing plants without soil and has been practiced for many years Hydroponic systems for growing flowers, fruit, and vegetables in a controlled environment and without use of soil has been practiced in over 10 known applications over the last 40 years Generally, controlled hydroponic systems for the production of complex plants such as commercial flowers or vegetables comprise a controlled environmental enclosure in which plants are germinated and grown on trays. The enclosure is usually a conventional greenhouse. A structure is formed with a steel skeleton, the skeleton then being covered with panes of transparent glass or plastic to allow sunshine onto the plants to allow photosynthesis. Most of these applications also include some type of air conditioning (whether heating or cooling) and distribution system, a water supply and irrigation system, and may also include artificial light sources to enhance light available to the plants.

These types of traditional photobioreactors are simply not commercially viable for mass production of algae, Cyanobacteria, and other microorganisms. They are not cost effective in producing large quantities of high quality. Because the structures are simply too expensive to construct at sufficient size, and as opposed to more valuable crops such as vegetables and flowers, algae simply does not have a sufficiently high margin to justify such production.

Because no efficient large-scale photobioreactors had yet been available, open cultivation ponds and clear tubes and tank systems have been used for almost all commercial algae production (generally for use as food additives). However, it is difficult to obtain high productivity in open ponds because the temperature and light intensity vary throughout the day and year and tube and tank systems are costly to construct and maintain. In addition, open ponds require a large surface area, and problems with contamination arise.

It is therefore desirable for a large-scale photobioreaction to be economically feasible for the purposes of mass-producing algae, Cyanobacteria, and other microorganisms from which biofuel may be derived.

SUMMARY

The following is a summary of the invention in order to provide a basic understanding of some aspects of the invention. This summary is not intended to identify key or critical elements of the invention or to delineate the scope of the invention. The sole purpose of this section is to present some concepts of the invention in a simplified form as a prelude to the more detailed description that is presented later.

Because of these and other problems in the art described herein, among other things, is a system for hydroponically growing, harvesting, processing and distributing photosynthetic microorganisms and their by products comprising: a self-contained growing enclosure, further comprising: an air supported structure, further comprising a skeleton, a membrane placed over said skeleton in a manner designed to be permanent, and a grid system affixed to said skeleton; a control compartment, further comprising a plurality of storage tanks and controls for said system, wherein at least a first storage tank of said plurality of storage tanks contains a liquid medium, at least a second storage tank of said plurality of storage tanks contains microorganisms, and at least a third storage tank of said plurality of storage tanks acting as a mixing tank within which said liquid medium is mixed with said microorganisms in predetermined quantities to form a slurry; a plurality of cradles capable of receiving said slurry through an inlet end, and permitting harvest of said microorganisms through an outlet harvest end; wherein said plurality is vertically racked; and wherein said plurality permits said slurry to move from said inlet end to said outlet harvest end in a manner that permits growth of said microorganisms; a handling system capable of conveying carbon dioxide and predetermined quantities of material stored within said storage tanks to at least one cradle of said plurality of cradles; and means for distributing carbon dioxide to a section of said inlet end of at least one of said plurality of cradles.

In an embodiment of the system said structure is maintained by a mechanical operating system, comprising a fan, a heater, and a cooling element and said means for distributing is a perforated tube present along said cradle's length and an air handling and conditioning system.

In an embodiment of the system said enclosure further comprises means for making available a continuous conditioned and filtered air flow across all of said cradles.

In an embodiment the system further comprises a light source capable of radiating light from under said cradles to said microorganisms. Such light source may comprise a tube structure enclosing a plurality of light bulbs and affixed on said cradles' underside, and wherein said underside is translucent or transparent.

In an embodiment of the system said microorganisms are algae or bacteria and said liquid medium comprises substances derived from an excess, including but not limited to a sewerage excess or a farming excess and water.

In an embodiment of the system the movement of said slurry is aided by gravity. The membrane may be an outer membrane, and said structure further comprises an inner membrane.

In an embodiment, the system further comprises means for harvesting by froth floating, flocculating, dissolved air floating, or centrifuging and means for processing by centrifuging or homogenizing.

In another embodiment of the system the controls automate said mixing of said slurry, said receipt of said slurry, said movement of said slurry, operation of said handling system, operation of said means for harvesting, and operation of said means for processing.

There is also described herein, a method of providing beneficial by-products of photosynthetic microorganisms, the method comprising: having a self-contained growing enclosure, comprising an air supported structure further comprising a membrane; installing a racking system, comprising racked cradles, within said enclosure; mixing a predetermined quantity of liquid medium from a first storage means with a predetermined quantity of said microorganisms from a second storage means to form a slurry; placing said slurry in a predetermined number of said cradles at an inlet end of said cradles; distributing carbon dioxide to said cradles; causing said slurry to flow from said inlet end to an outlet harvest end of said cradles in a manner that permits multiplication of said microorganisms, making available a continuous conditioned and filtered air flow across all of said cradles; harvesting said microorganisms at said outlet harvest end; and processing said microorganisms to obtain molecules useful in fuel, wherein said microorganisms are separated into oil and solids, and further processing said microorganisms for other by products including, but not limited to bio diesel, animal feed, fertilizer, pharmaceuticals and the like.

In an embodiment the method further comprises radiating light from under said cradles to said microorganisms, which may be algae or bacteria.

In an embodiment of the method, the placing or causing may aided by gravity, such as by positioning the cradles at about a 1 to 5 degree angle.

In another embodiment of the method, the carbon dioxide is drawn from a storage means.

In another embodiment of the method, the making is performed by an air handling and conditioning system.

In another embodiment of the method the liquid medium comprises substances derived from farming excess and water. The membrane may also be an outer membrane, and said structure further comprises an inner membrane, a skeleton, a grid system affixed to said skeleton and support for maintaining said structure further comprising a fan, a heater, and a cooling element.

In a still further embodiment of the method, the distributing is performed by a perforated tube present along said cradles' length, the harvesting comprises froth floating, flocculating, dissolved air floating, or centrifuging, and the processing comprises centrifuging or homogenizing.

In a still further embodiment of the method the mixing, placing, distributing, causing, making, harvesting, and processing are continuously repeated and may be automatically controlled.

There is also described herein a method of hydroponically growing photosynthetic microorganisms comprising: deriving a liquid medium; storing said liquid medium in a first storage means; storing microorganisms in a second storage means; mixing a predetermined quantity of said liquid medium from said first storage means with a predetermined quantity of said microorganisms from said second storage means to form a slurry, wherein said slurry is stored in a third storage means that is in fluid communication with said first storage means and said second storage means; storing carbon dioxide in a fourth storage means; having a self-contained growing enclosure, comprising a structure further comprising a membrane; installing a racking system, comprising racked cradles, within said enclosure, wherein said racking system is in fluid communication with said third storage means, and said fourth storage means; placing said slurry in a predetermined number of said cradles at an inlet end of said cradles; distributing a predetermined quantity of said carbon dioxide from said fourth storage means into said cradles via said fluid communication; causing said slurry to flow from said inlet end to an outlet harvest end of said cradles in a manner that permits multiplication of said microorganisms; making available a continuous conditioned and filtered air flow across all of said cradles; conveying said microorganisms from said outlet harvest end to a means for harvesting; harvesting said microorganisms with said means for harvesting, and processing said microorganisms by separating said microorganisms into oil and solids, and further processing said microorgan-
isms for other by products including, but not limited to bio diesel, animal feed, fertilizer, pharmaceuticals and the like.

In an embodiment of the method, the harvesting comprises froth floating, flocculating, dissolved air floating, or centrifuging and the processing comprises centrifuging or homogenizing. In a further embodiment the method further comprises transportation, distribution and conveyance of components or by products for further processing.

In an embodiment, the method further comprises radiating light from under said cradles to said microorganisms which may be algae or bacteria.

In another embodiment of the method the liquid medium comprises substances derived from an excess, including but not limited to a sewerage or a farming excess and water.

In another embodiment of the method said steps of mixing, placing, distributing, causing, making, harvesting, processing and distributing are continuously repeated, may be automatically controlled, and may be performed at co-located facilities and at distal locations.

In a still further embodiment, the structure is supported by frames, airbeams or another form of support, or may be a tension-supported structure.

DESCRIPTION OF THE PREFERRED EMBODIMENT(S)

Figure 1:
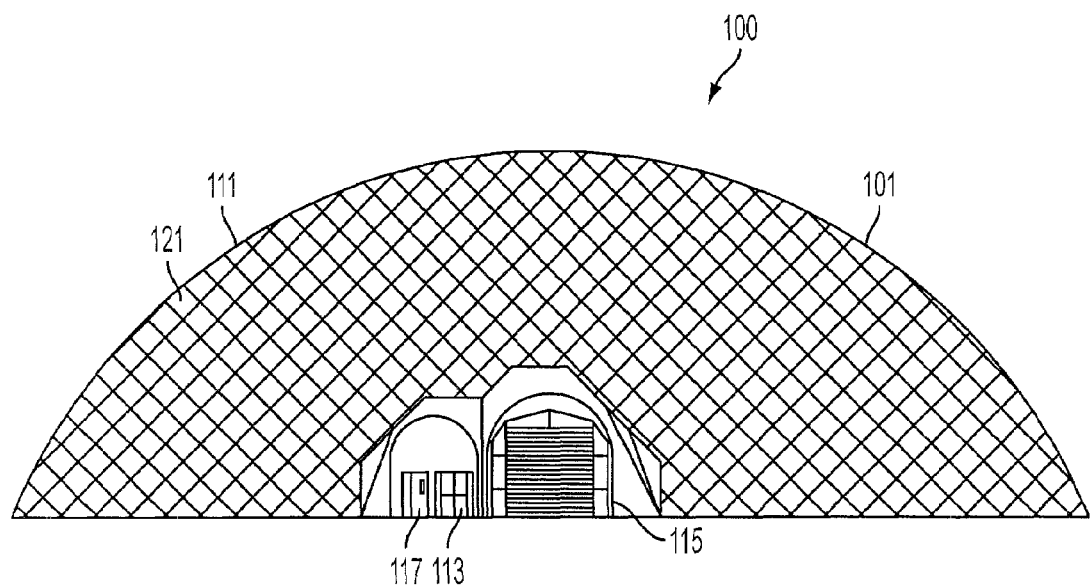
FIG. 1 is a front elevational view of an embodiment of a hydroponic growing enclosure.
Figure 2:
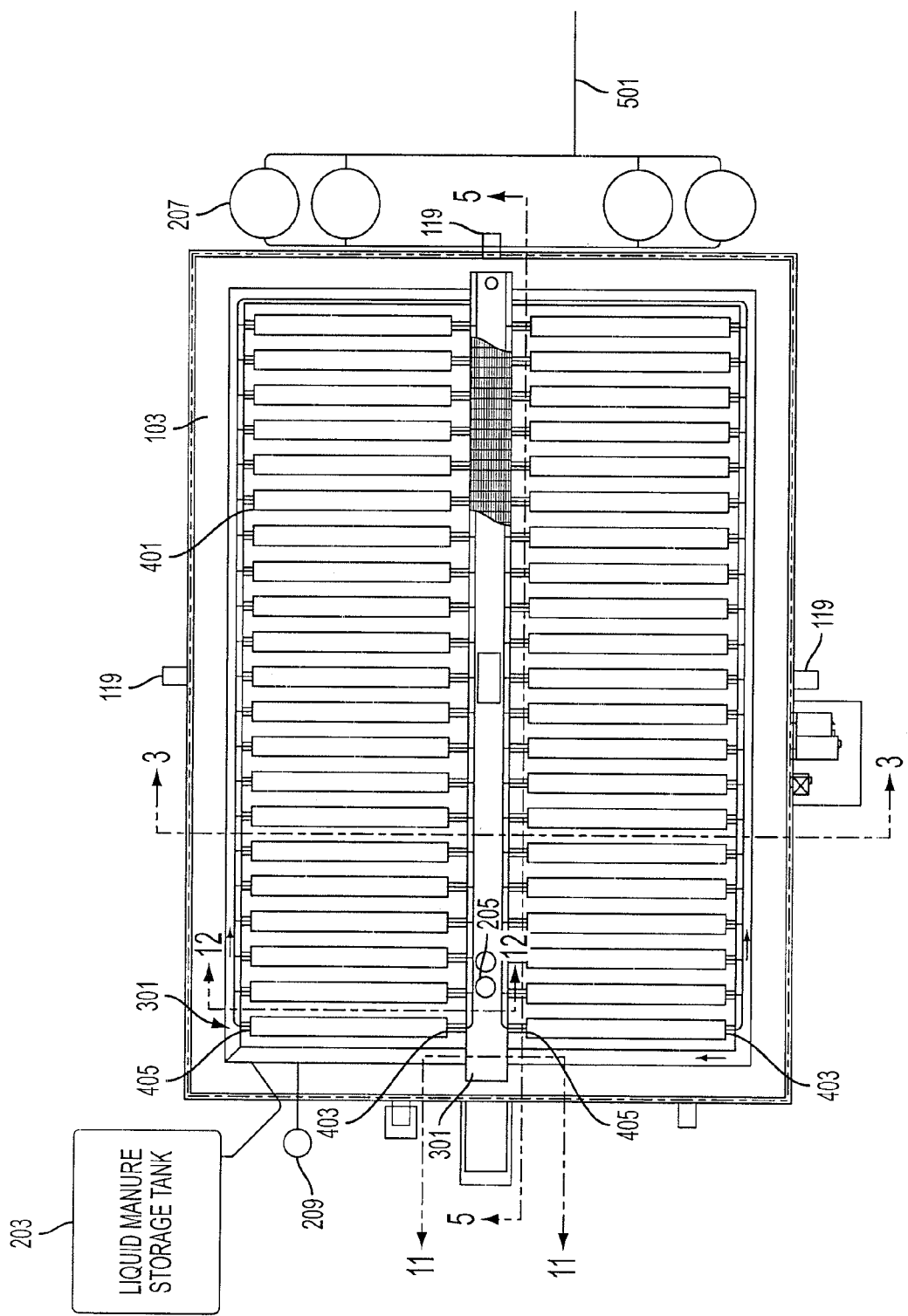
FIG. 2 is a floor plan of another embodiment of a hydroponic growing enclosure similar to that of FIG. 1.
Figure 3:
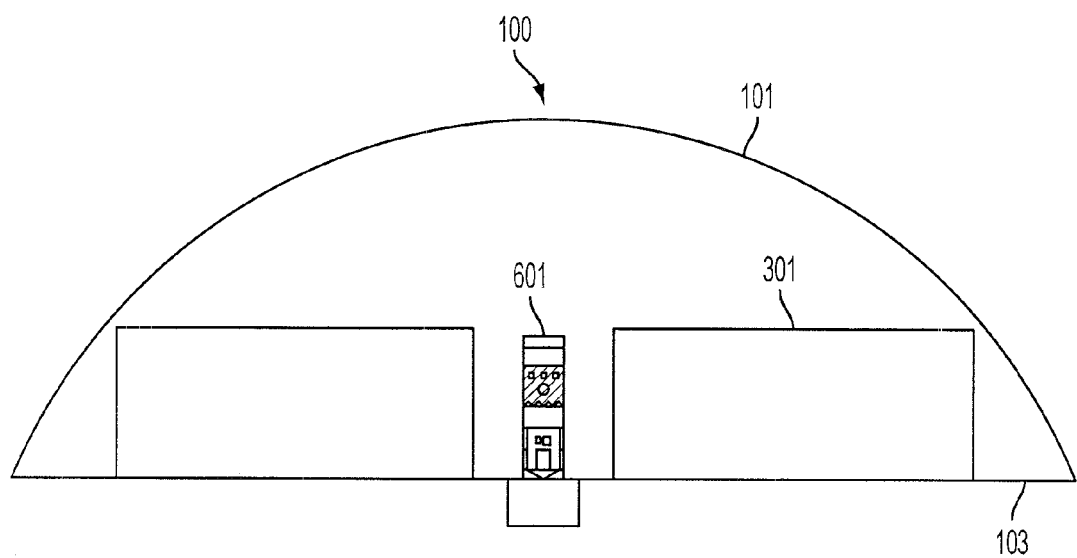
FIG. 3 is a simplified sectional side view of the embodiment of FIG. 2 along line 3-3.
Figure 4:
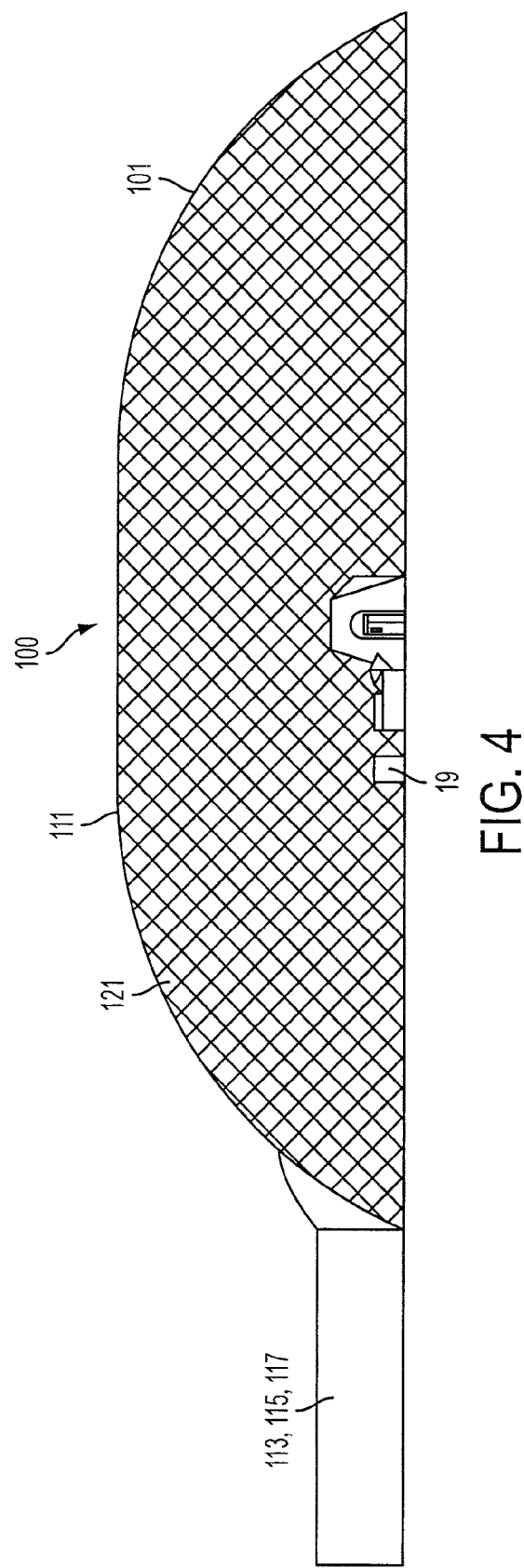
FIG. 4 is a side elevational view of the enclosure of FIG. 1.
Figure 5:
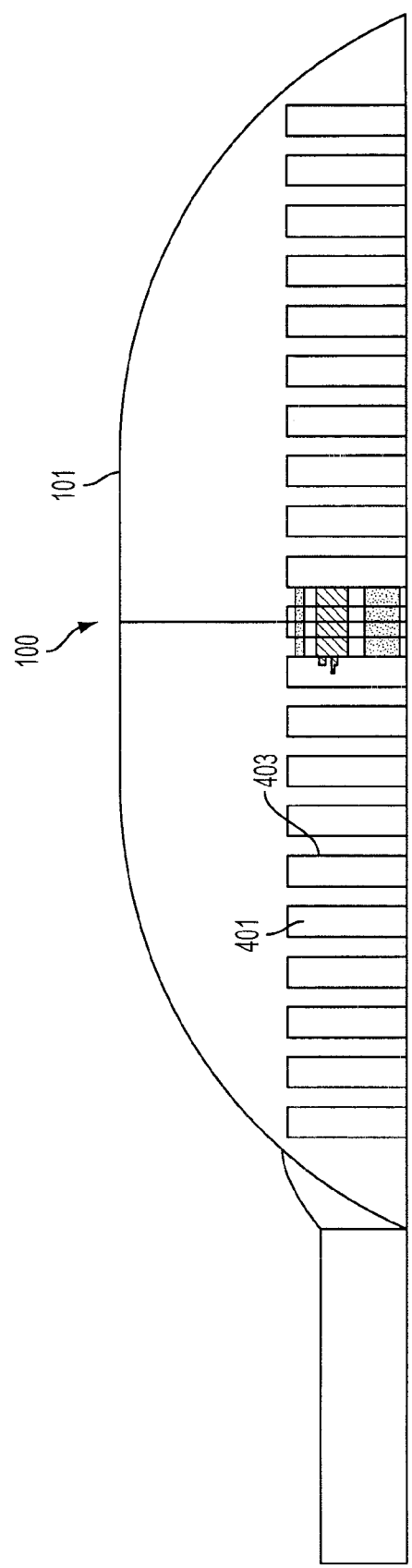
FIG. 5 is a simplified sectional view of the enclosure of FIG. 2 along the line 5-5.

Throughout this disclosure, the microorganisms being described will be referred to as algae. This is to provide for an exemplary organism. As would be understood by one of ordinary skill in the art, the discussion of growing algae can be applied, without undue experimentation, to the growing of Cyanobacteria or other similar microorganisms. Further, the systems and methods discussed herein do not provide for any particular type(s) of algae to be grown and harvested. This is because it is expected that any desired algae(s) may be grown, harvested and processed, and by products distributed.

FIGS. 1 through 5 provide various views of a structure (101) and growing enclosure (100) which may be utilized in an embodiment of the invention, generally comprising five main components which relate to general aspects of the operation of the enclosure (100) in growing of the algae. The primary component is a housing structure (101) which serves to isolate the algae and growth process from the external environment.

The second component is a control compartment including storage tanks (203) designed to contain a liquid medium which will serve as a growth material for the algae. The liquid medium will generally include water, liquefied animal waste, and/or other fertilizers. The control compartment will also include control elements of the various devices and the structure itself. It may also include various tanks for storing algae prior to (205) and after (207) harvesting.

The third component is a handling system for conveying carbon dioxide, the liquid medium and a starting growth of algae in the form of spores, seeds or related structures from the storage tanks to a plurality of cultivation and growing cradles (401). The handling system will comprise pipes, wiring, and similar components which are generally placed in a covered utility trench (301) in the base (103) of the structure (101).

The fourth component is the cradles (401) themselves. The cradles (401) serve to contain the liquid medium and algae and provide it with access to light and air. The cradles (401) are generally arranged in a generally racked form and are capable of holding the liquid medium. Generally the cradles (401) have an inlet end (409) for input of the liquid medium, algae, and distribution of carbon dioxide and an outlet harvest end (411) where, once the algae has developed to the prerequisite mass they can be harvested.

The fifth component of the system comprises the harvesting, processing, conversion and distribution of the raw algae into the desired by products or substance such as biofuel which is then stored, distributed and further processed at the same or a distal location. In an embodiment, once it is grown, the algae will generally be removed from the building via gravity flow and may be mechanically separated from the growth medium by piping (501) the resulting algae to a centrifuge or similar device. Both the growth medium and the algae may then be processed in any manner known to one of ordinary skill in the art to produce desired outputs.

In an embodiment, the enclosure (100) is used as part of a method of hydroponically growing photosynthetic organisms within the enclosure (100) and independent of outside climatic conditions, said method comprising the steps of: mixing a predetermined quantity of liquid medium from a storage means with a predetermined quantity of photosynthetic microorganisms such as algal spores or the like; placing the resultant slurry in a predetermined number of transparent growing cradles (401) at an inlet end (409) of a racking system such as through the use of gravity, this placement may be by weight or other manner; radiating light from under the cradles (401) to the microorganisms; circulating a continuous conditioned and filtered air flow across all of said cradles (401) supported in said racking system from said inlet end (409) to an outlet harvest end (411); and distributing carbon dioxide generated or from a storage means (209) to said cradles. This may be repeated in a continuous fashion to provide for a constant growth of microorganisms.

The growing enclosure (100) generally comprises a liquid medium storage tank (203) located as part of a control compartment section of the enclosure (100) and preferably isolated from a growing and harvest compartment section. The liquid medium will comprise some mixture of water and nutrients which may be provided organically or synthetically. In an embodiment, the liquid medium comprises some form of black or gray water and may include human or animal waste. In an embodiment, the liquid medium is liquefied sewerage, animal manure, forest or mill residuals, and/or spoiled animal feed, such as is provided from the output of an anaerobic digester or related structure. Such a liquid medium accomplishes the goal of productively using excess such as sewerage or farming wastes like excess feed and fertilizer.

Pipes (307) convey the liquid medium from a storage tank (203) to a mixing tank (205). Here the liquid medium is mixed with algae, algal spores or related materials to produce a slurry suitable for algal growth. The slurry is then provided by piping (303) to the input end (409) of a cradle (401). The cradles (401) are generally provided in a racking system in the growing and harvest compartment to support a plurality of layers for cultivating the algae in horizontally spaced-apart arrangement. Each cradle in the racking system has an inlet end (409) where the liquid medium/algae mix is input and extends along a length where the algae is growing until reaching a terminal end (411) where algae is harvested.

In alternative or single embodiments, each, some, or all of the mixing tank (205), pipes (307), and liquid medium storage tank (203) are co-located with the enclosure. In further embodiments, these components (205, 307, 203) may be located within the enclosure (100), on an adjunct, or as part of a wing thereof. In a further embodiment, the tanks (203, 205) and pipes (307) may be located in the growing and harvest compartment of the enclosure (100). Such co-located embodiments enable the processes disclosed herein to be conducted efficiently, without the costs and risks of transport between facilities, but are by no means required and in alternative embodiments, such facilities may be located at disparate locations. Such risks of disparate location may include damage to the microorganisms, contamination of transported substances, miscommunication between origin and destination facilities, or inevitable delays in transport (i.e., due to weather) that interrupt the processes disclosed herein.

The cradles (401) preferably are placed in close proximity to a perforated tube (410) which runs the length of each cradle (401) and, in an embodiment, may protrude (412) into the internal volume of the cradle (401). The tube (410) serves as a gas distribution system distributing carbon dioxide along the length of the cradle (401). Light units (700) are provided in an embodiment in conjunction with the cradle (401). The light units are preferably dimensioned to provide light over all of the liquid growing medium and to the algae. An air handling and conditioning system (601) having directional air outlet means is provided for recirculating the carbon dioxide gas and for circulating air in the enclosure (100). A water supply conduit (305) may also be supplied to the enclosure (100) to connect with an external pressurized water supply source for maintenance.

In the depicted embodiment, the enclosure (100) is preferably an air supported structure (101) a frame-supported structure, or a structure which can be used to maintain the environment at desired levels, fabricated from vinyl coated polyester, with an inner liner of an insulating material, whereby the enclosure can be temperature-controlled to facilitate growth of photosynthetic organisms independently of outside climatic conditions. The structure (101) may be assembled on site by the use of conventional tools.

As the structure (101) is air supported, it can be of virtually any size and it is generally preferred that the structure (101) be of significant size so as to facilitate economies of scale. In an embodiment, it may be 10' by 10' by 30' long. An air supported structure (101) has a number of advantages in this application due to its ability to support its own weight regardless of resulting size or shape. It is preferred that membrane (111) of the structure (101) be light permeable, at least in the wavelengths of light used by the algae for photosynthesis. It is also preferred that membrane (111) be resistant to ultraviolet light degradation.

It is preferred that the self-contained hydroponic growing structure (101) include an insulated fabric membrane (111) forming its principle structure to provide for outdoor use and continuous operation under outside climatic conditions ranging from about −40 degrees Fahrenheit to at least +100 degrees Fahrenheit without significant attention to its internal temperature. In an embodiment, the membrane (111) is white, may be translucent, and made of a variety of architectural material, including but not limited to, DACRON™. It is preferred that the membrane be fire resistant in accordance with applicable regulations. In an embodiment, the membrane (111) weighs between about 28 and about 30 ounces per square yard.

To provide temperature control in an embodiment, a vinyl-coated, translucent, polyester second layer (not shown) may be constructed onto the outer membrane (111), creating a dead-air space of generally 6-12". In an embodiment, this second layer may weigh 14 ounces per yard, and may also be fire resistant. This results in a minimum cost of heating and/or air conditioning the structure and provides for installing fiberglass or other insulating materials, if desired. The second layer and air space may also serve as an acoustical barrier. In an embodiment, the second layer is attached using a perpendicular "tab" detail to attach the inner and outer fabric allowing for 100% insulation. In such an arrangement, when the inner and outer fabric meet there are generally no condensation problems or interruption in the dead, insulated air space.

In an embodiment, the structure (101) is temporary. It may be formed from a skeleton made of synthetic materials, supported by air, aluminum, steel or other frames, or any combination thereof. In a further embodiment, the skeleton comprises a plurality of airbeams, which may be formed as is known in the art by covering an air bladder with three-dimensional woven fabric, or by any equivalent means. In an alternative embodiment, the skeleton comprises a tension-supported structure made of cables. Any form of skeleton which provides a sturdy, relatively temporary structure is contemplated. The air structure generally develops its structural integrity from an internal air pressure provided by an air handling unit and/or air rotation unit (601), which replaces natural air loss throughout the structure (101). The structure (101) is anchored to a concrete grade base (103), or directly to the earth via earth anchors. The anchors can be permanent, temporary or a seasonal installation.

On the skeleton is placed the fabric membrane (111) generally comprising of a vinyl-coated polyester weave, which is available in a number of translucent or transparent colors. It is preferred that the membrane (111) be capable of transmitting light in a wavelength used for photosynthesis by the organisms in the enclosure (100). However, natural light is not required and photosynthesis can occur by entire illumination from artificial light. Custom fabrics, such as camouflage for military applications, are also available.

The membrane (111) may be sewn together, heat sealed, ultrasonically welded, adhered or otherwise connected and held together. It is, however, preferred that membrane components be connected by electronic radio frequency (RF) welding which develops seam construction equal to the fabric or material strength. This generally increases the life of the structure (101), prevents undesirable air loss, and eliminates costly maintenance and repair. Openings for human access doors (113) and (117), vehicle airlocks (115), blowers, heaters or air conditioning are placed in the structure in a preferably tension-free arrangement.

The structure (101), in an embodiment, is further provided with a grid system (121) which prevents movement of the structure (101) in high winds and decreases stress on the membrane (111), increasing safety factors and extending the life and usability of the structure (101). In an embodiment, the grid system (121) comprises vinyl-coated, galvanized, cable which is non-abrasive and designed to exceed the industry's basic cable systems safety factors, providing the structure (101) with performance to equal, or exceed, that required by local structural requirements.

In an embodiment, the enclosure (100) is maintained by a mechanical operating system which may comprise a combination of specially manufactured fans, heat exchanger and related burner, cooling coils and condensing unit, operating controls and many other accessories and options, including emergency and back-up generators and blowers.

Entrance into and out of the structure (101) may be through any number of doors (113), (115) and (117). Generally these doors (113), (115) and (117) will be chosen to provide for a relative air seal so that there is minimum loss of air from inside the enclosure (100). The doors (113), (115), and (117) may comprise any type of door including air lock double doors (117) or revolving doors (113) and may be sized and shaped to accommodate various types of traffic including vehicular airlocks (115) to provide access for forklifts or full-length tractor-trailers. Revolving doors (113), personal airlocks (117), and emergency exit doors (119) for entering and exiting under all conditions can be provided for human personnel.

The structure (101) will generally be clamped down, in most cases to a concrete foundation (103) that is designed to take the structure (101). Alternatively, the structure may have earth anchors if designed for temporary use or smaller size.

The enclosure (100) includes a control compartment section generally external to the structure. The control compartment section may house two hopper tanks (203) which are fed liquid medium by means of pipes. The pipes will generally connect to a co-located source of the medium, or may alternatively be used to pipe in liquid medium from a remote location, or to unload trucks, rail cars, or other vehicles transporting the liquid medium. There is also included a tank holding the photosynthetic organisms (205) spores or seeds which are to be introduced to the liquid medium as needed when provided to the cradles (401). The control compartment may also house a water tank (not shown) which is connected by suitable piping (305) to various components of the system in the event water is needed. A heater (not shown) may be provided to maintain the temperature of the liquid medium during cold climatic conditions outside the structure (101).

In an embodiment, a central system serves the self-contained hydroponic growing enclosure wherein the water feed system, as well as the air handling system and carbon dioxide system, are automatically controlled eliminating the need for human workers to perform routine tasks.

Figure 7:
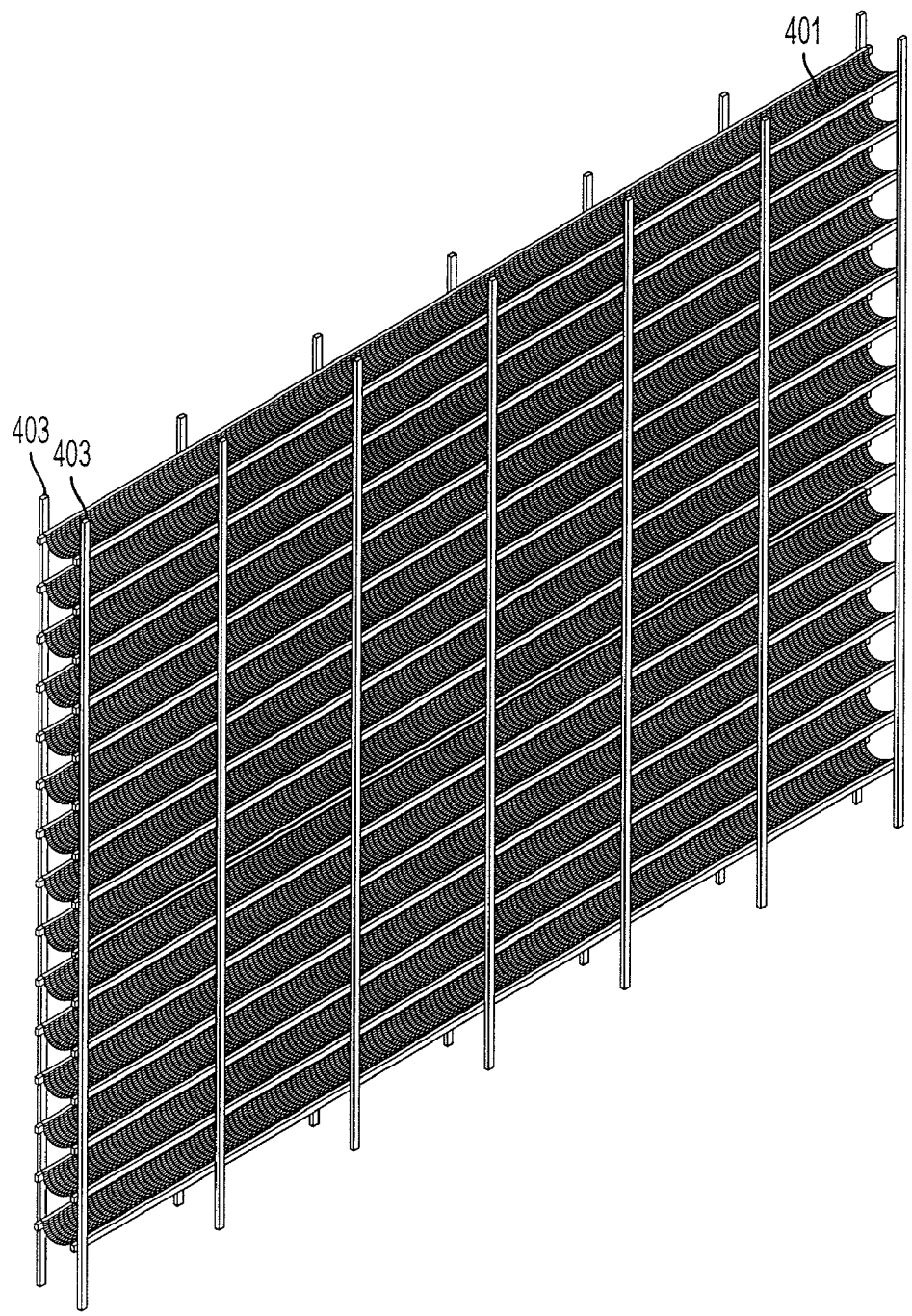
FIG. 7 is a perspective view of an embodiment of a cradle racking system.
Figure 8A:
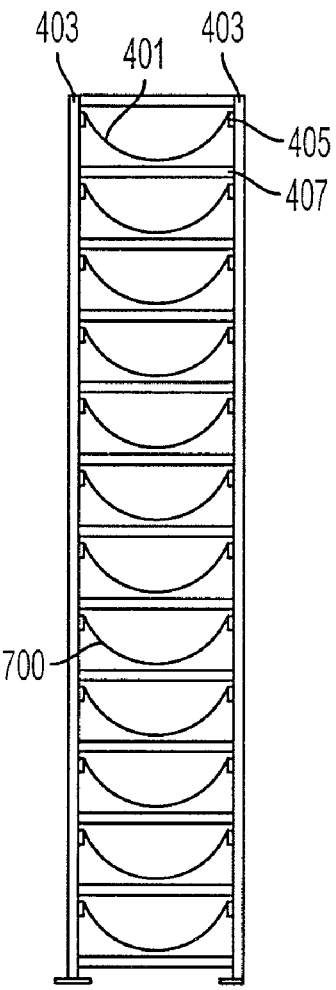
FIGS. 8A and 8B are sectional views showing alternative embodiments of the cradle racking system.
Figure 8B:
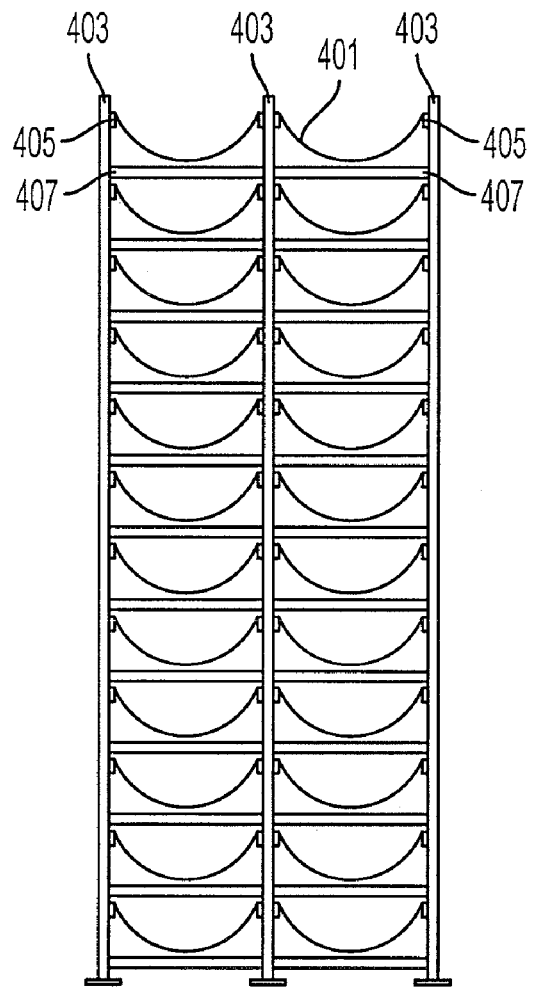

In an embodiment, the enclosure (100) utilizes growing surfaces comprising cradles (401). The cradles (401) will generally be open air, having a troughlike structure, but alternatively may be enclosed. In the depicted embodiment of FIGS. 7 and 8, the cradles (401) are formed into a racking system which comprises a plurality of vertical spaced apart frame members (403), support members (405) secured to said vertical frame members for securing plastic cradles (401), the support members being inclined downward from said inlet end to said outlet harvest end for gravity feed of cradles (401)

supported on the racks, stiffening members (407) for improved strength of the racks, and the cradles (401) themselves. The racks may hold a single row of cradles (401), as in FIG. 8A, or multiple rows, an embodiment of which is depicted in FIG. 8B.

The support members (405) may be strings or supportive netting extending beneath and along the width of the cradle (401); fasteners on either side of the cradle (401), such as clamps, screws, or adhesive; a receptive trough into which the cradle (401) nests; or any other means known in the art.

The vertical stacking of the cradles (401) allows for a large volume in which to grow the microorganisms, without requiring a large footprint for the enclosure (100). The extent of vertical stacking is limited only by the desired height of the enclosure (100), as slurry introduction and harvesting can be conducted regardless of the cradle's (401) height, and there are no structural limitations on the racking system's height. Due to the translucence of the membrane (111) forming the "walls" of the enclosure (100), cradles (401) lower on the racking system still receive adequate light for the microorganisms in those cradles (401) to photosynthesize. In embodiments in which light sources are fixed to the underside of the cradles (401), cradles (401) lower on the racking system have their light supplemented in the event higher cradles (401) cast shadows over those lower cradles (401).

Figure 9:
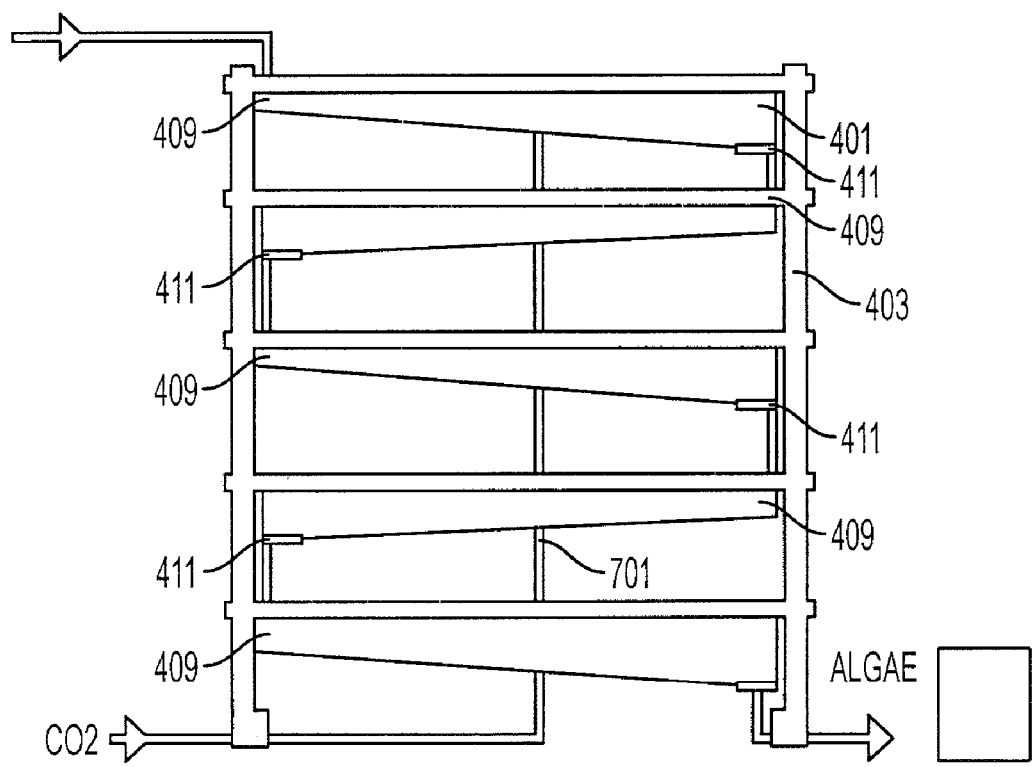
FIG. 9 is a perspective view of an alternative embodiment of a cradle racking system.

FIG. 9 illustrates an embodiment of the downward slope of the cradles (401). The downward angle slopes from the inlet end (409) to the outlet harvest end (411) at preferably about a 1 to 5 degree angle, more preferably a 2 degree angle. This provides for ease of harvesting by gravity as the slurry is pushed from the inlet end (409) for reloading with fresh liquid medium and algae from the mixing tank (205).

In an alternative embodiment, shown in FIG. 9, cradles (401) within a rack may be in fluid communication, through connective piping, alternating downward slopes, or any other means. Such an embodiment may be useful where algae need a longer time to grow than is afforded by the time it takes the slurry to travel down one cradle (401); it may also be preferred where an enclosure's (100) width is limited. In such an embodiment, a cradle's (401) input end (409) is defined by slurry entry, and the output harvest end is defined by slurry exit, even though harvesting may not occur upon that exit.

As shown in the depicted embodiment, the racking system is secured over a drainage floor, which is inclined to channel water to a discharge conduit to direct any spillage toward a drain or otherwise out of the structure. As previously described, there may be water tanks (not shown) constituting a reservoir means for supplying water for maintenance.

Figure 11:
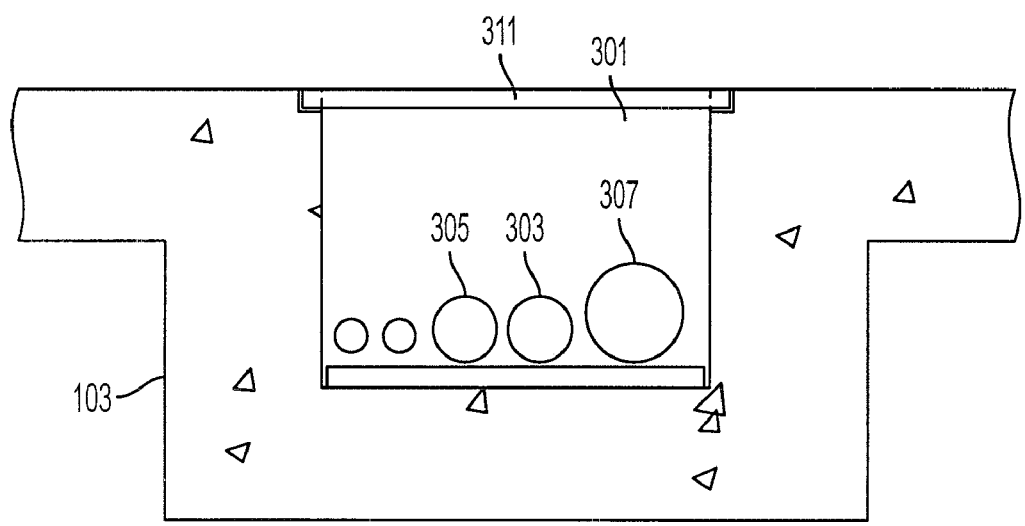
FIG. 11 is a simplified sectional view along the line 11-11 of the enclosure of FIG. 2 showing the utility trench.
Figure 12:
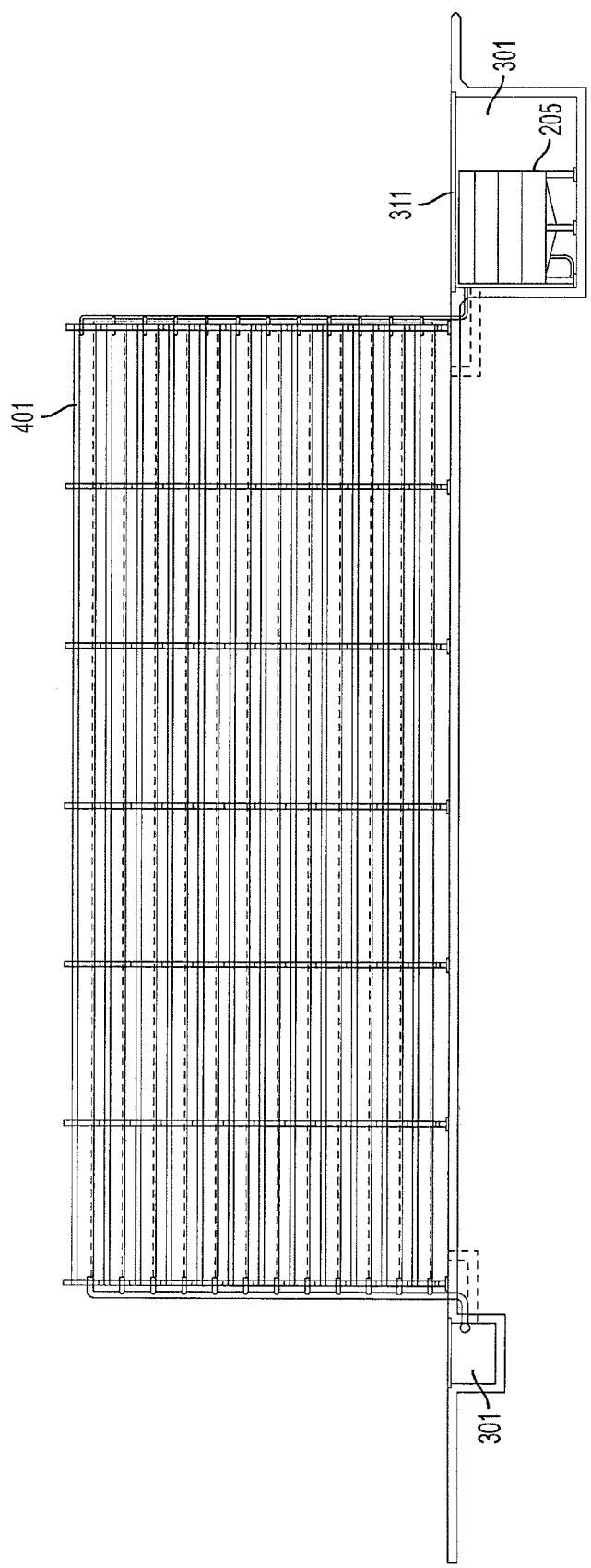
FIG. 12 is a simplified sectional view along line 12-12 of the enclosure of FIG. 2.

The liquid medium and algae slurry is fed into the cradles (401) at an input end (409). Generally, a feeding will occur to keep the amount of slurry in the cradles (401) relatively constant. The gravity feed may also serve to move various items outside the cradles (401). As shown in FIG. 11, the base (103) of the structure (101) may include a trough (301) covered by a cover (311) and including various pipes and conduits as indicated.

The gravity racking system can be particularly useful as it can result in what amounts to a steady flow of algae and medium from the input end (409) to the harvest end (411) of the cradle (401). This can provide for displacing of the algae on a regular basis and in a manner which is easy to use for loading or unloading. In an embodiment, the algae effectively lives its growth cycle as it passes down the length of the cradle (401). As the slurry enters the cradle (401) gravity causes the cradle to fill. During the growing cycle, the algae starts to grow throughout the slurry in the cradle (401). When the algae is ready to be harvested, a valve or similar device at the harvesting end (411) is opened and gravity causes the algae and remaining liquid medium to exit the cradle (401) generally into outlet piping (307). It also begins to slowly be moved down the cradle (401) due to the force of gravity. This movement meets the algae's need for some turbulence and diffusion of nutrients. As the algae grows and increases its total mass, it slowly approaches the harvesting end (411). Eventually, the algal growth reaches the terminal end. This may be because the growth has reached a pre-selected mass or because a certain amount of time has passed.

At the final terminal end (411) the slurry is removed from the cradle (401) by any known harvesting means. The algae mixture is then piped out (307) of the structure and the algae is generally separated from the remaining liquid medium. In an embodiment, froth flotation separates algae from the medium by adjusting pH and bubbling air through a column to create a froth of algae that accumulates above liquid level. In another embodiment, flocculation causes small particles to join together to form larger particles which can be more easily filtered using less costly equipment. Further embodiments provide a continuous flocculation effect without the use of chemicals or additives. In another embodiment, dissolved air flotation separates algae from the medium using features of both froth flotation and flocculation. Alum may be used to flocculate an algae/air mixture, with fine bubbles supplied by air. Finally, in another embodiment, centrifugation separates algae from the medium. This causes the algae to settle to the bottom of the vessel. The liquid medium is disposed of in any understood fashion, or may be recycled into the cradles (401) if it is still sufficient for algae growth. The algae is provided to a processing system to be processed into desired by products or materials. In an embodiment, a percentage of algae may remain in each top cradle (401) to seed the next algae population.

In an embodiment, this processing system first separates the slurry into algae and water. A homogenizer as known in the art, which may be sonic, may then be used to rupture the cells. Algae components may then be separated from liquid by centrifuge. In an alternative embodiment, the algae slurry is first homogenized and then centrifuged to separate oil, water, and a high-protein algae paste. Water from any method may be returned to the holding tank (not shown). These processes may take place at the enclosure site or at a remote location. The algae components are then used to derive molecules useful in biofuel, in a manner known in the art or yet to be discovered.

Figure 10:
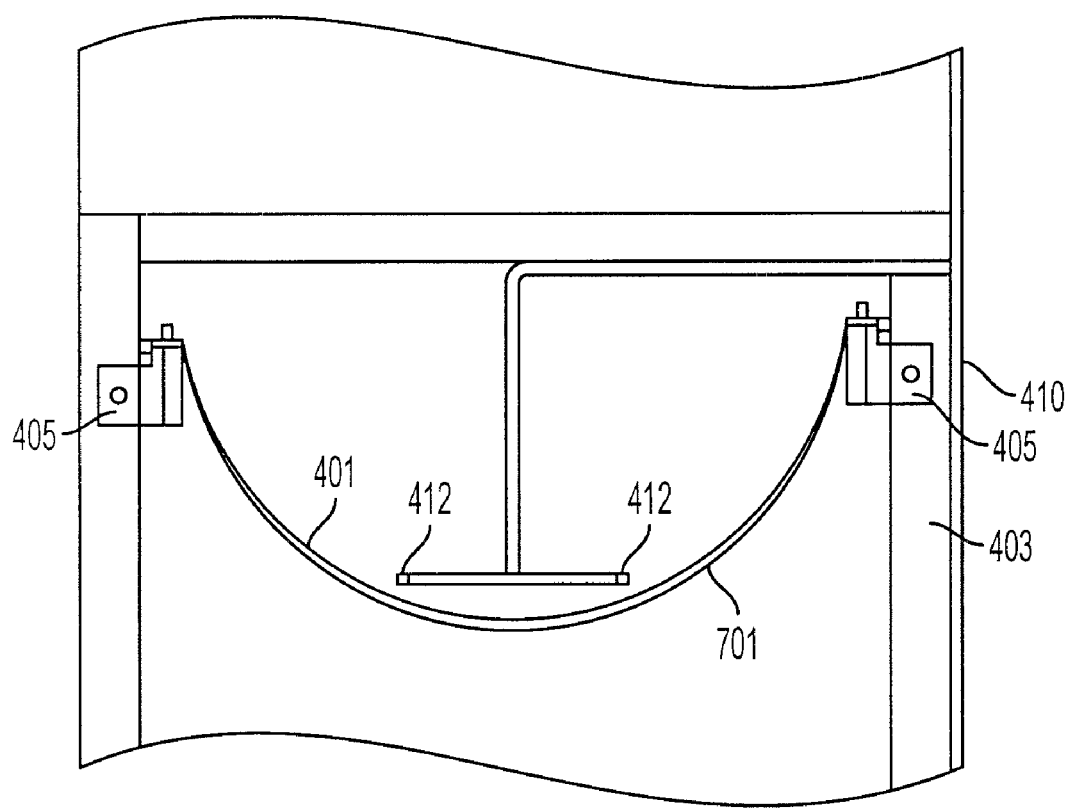
FIG. 10 is a sectional view showing an embodiment of a cradle with carbon dioxide and light supplied.

In an embodiment, light units (700) are placed in conjunction with the cradles (401) to provide for increased photosynthesis of the algae crop while it is in the cradle (401). The light may be used in place of, or in addition to, solar light made available to the algae. In one embodiment as depicted in FIGS. 8 and 10, the lights are placed on the undersides of the cradles (401) which are constructed of a translucent or transparent material to allow the light to be provided directly to each of the cradles (401) from the underside. Placing lighting on the underside of the cradle (401) can provide a number of advantages. Most importantly, the lighting can serve to provide light to a greater surface area of the liquid medium than sunlight can provide alone. This can allow for greater algal growth within the same volume of liquid medium. Providing artificial lighting to the algae can also supplement natural lighting by providing a greater intensity of useful wavelengths and/or by providing lighting in a constant fashion, that is, the artificial lighting can continue to provide light to the algae even when natural sunlight is not available, shortening the total required time for growth.

In an embodiment and as shown in FIGS. 8 and 10, the light arrangements (700) comprise light bulbs (701) arranged in strips wherein the light strips are each comprised of a tube structure, the housing being a waterproof tube structure (703) disposed along a horizontal cradle, said tube structure provides an even spectrum of light to said cradles (401). The light bulbs used may be of any type including filaments, arcs, Light Emitting Diodes (LEDs), Organic Light Emitting Diodes (OLEDs), fluorescent tubes, or other light structures.

Figure 6:
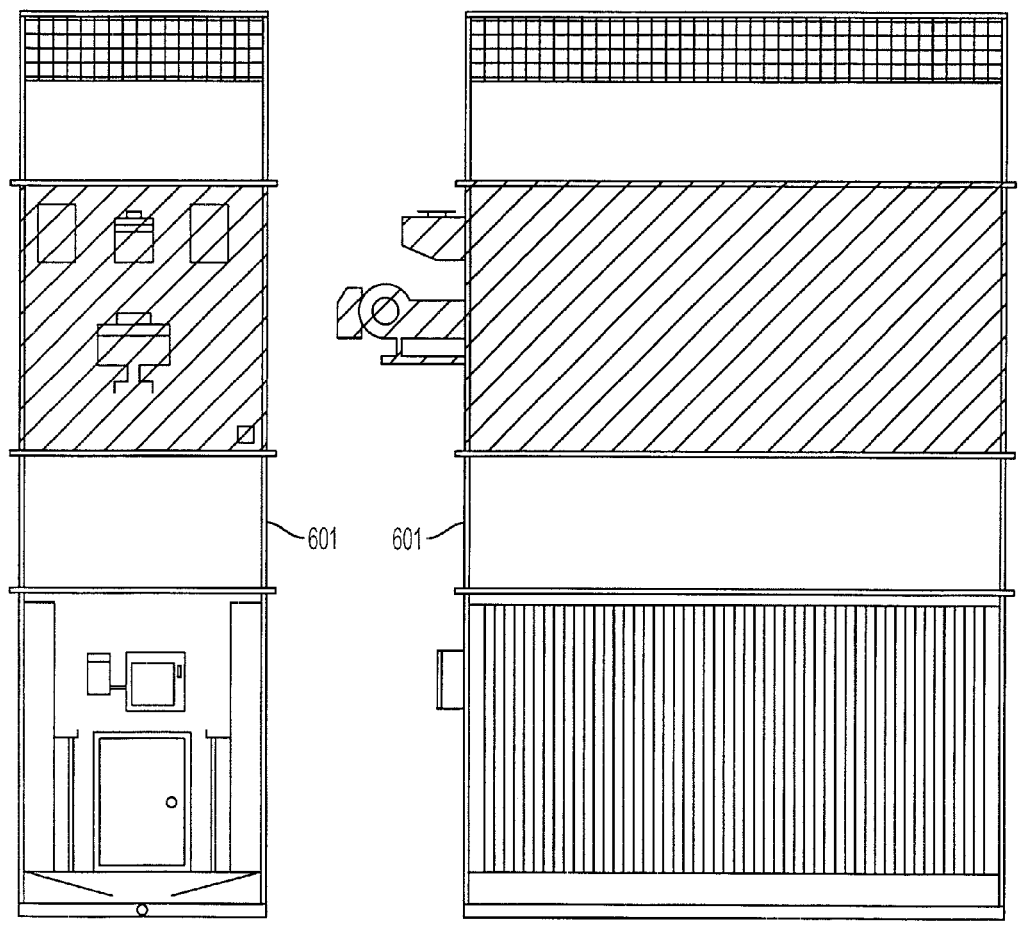
FIG. 6 provides a side and front view of an air handling unit.

As shown in FIG. 6, an air handling and conditioning system (601), including a mixing box section in an embodiment, circulates a continuous conditioned and filtered air flow across all of the trays supported in the racking system. This both provides a source of carbon dioxide and climate control, and can also serve to maintain the enclosure's (100) integrity. It is believed that temperature is particularly limiting on the growth of cultured algae, and so is regulated in an embodiment.

Figure 13A:
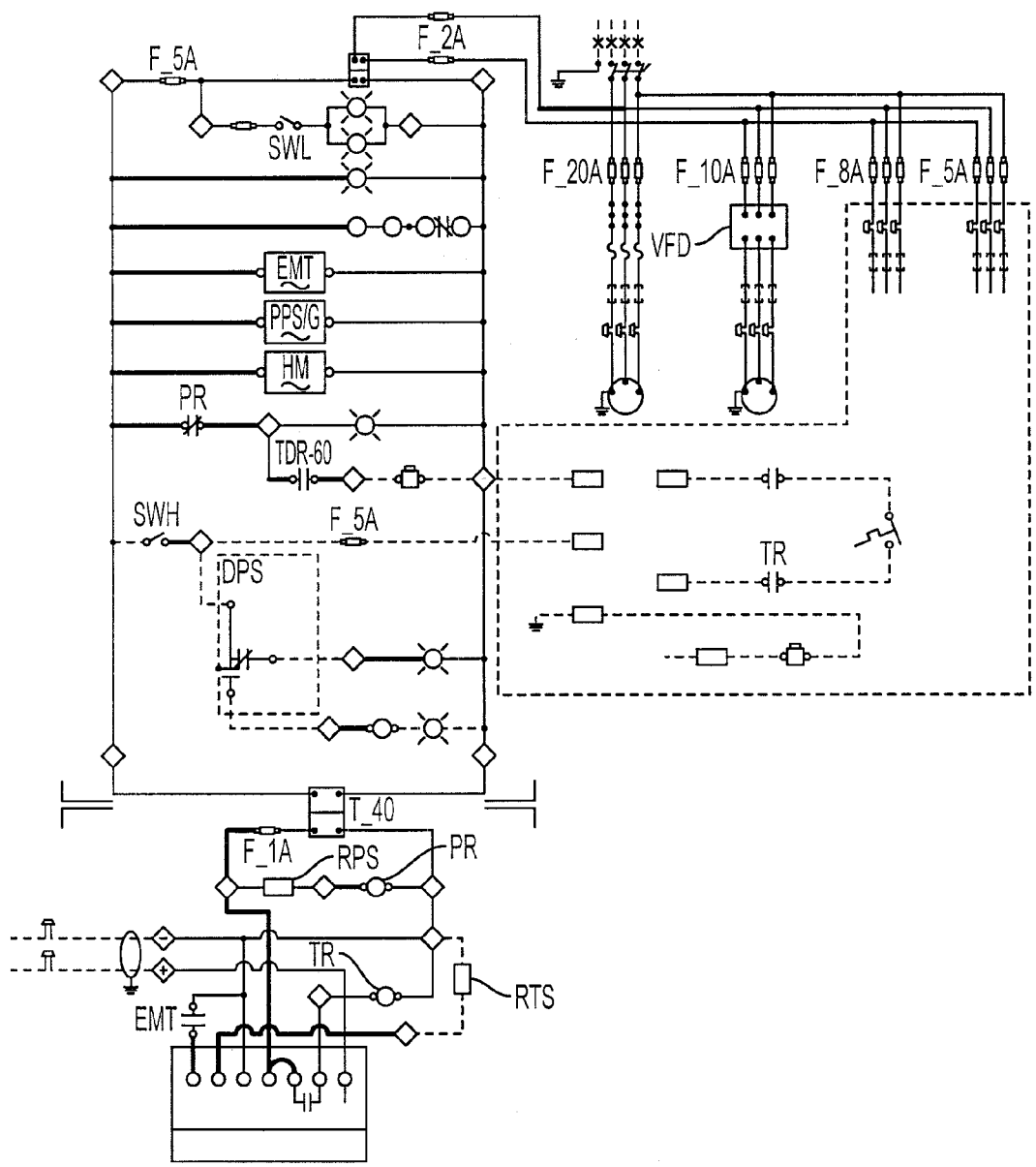
FIG. 13 is a circuit diagram of an embodiment of an air handling and conditioning system.
Figure 13B:
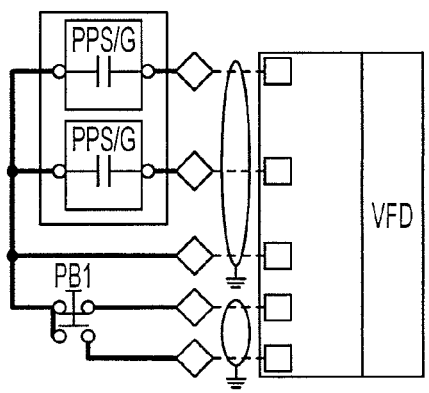
Figure 14:
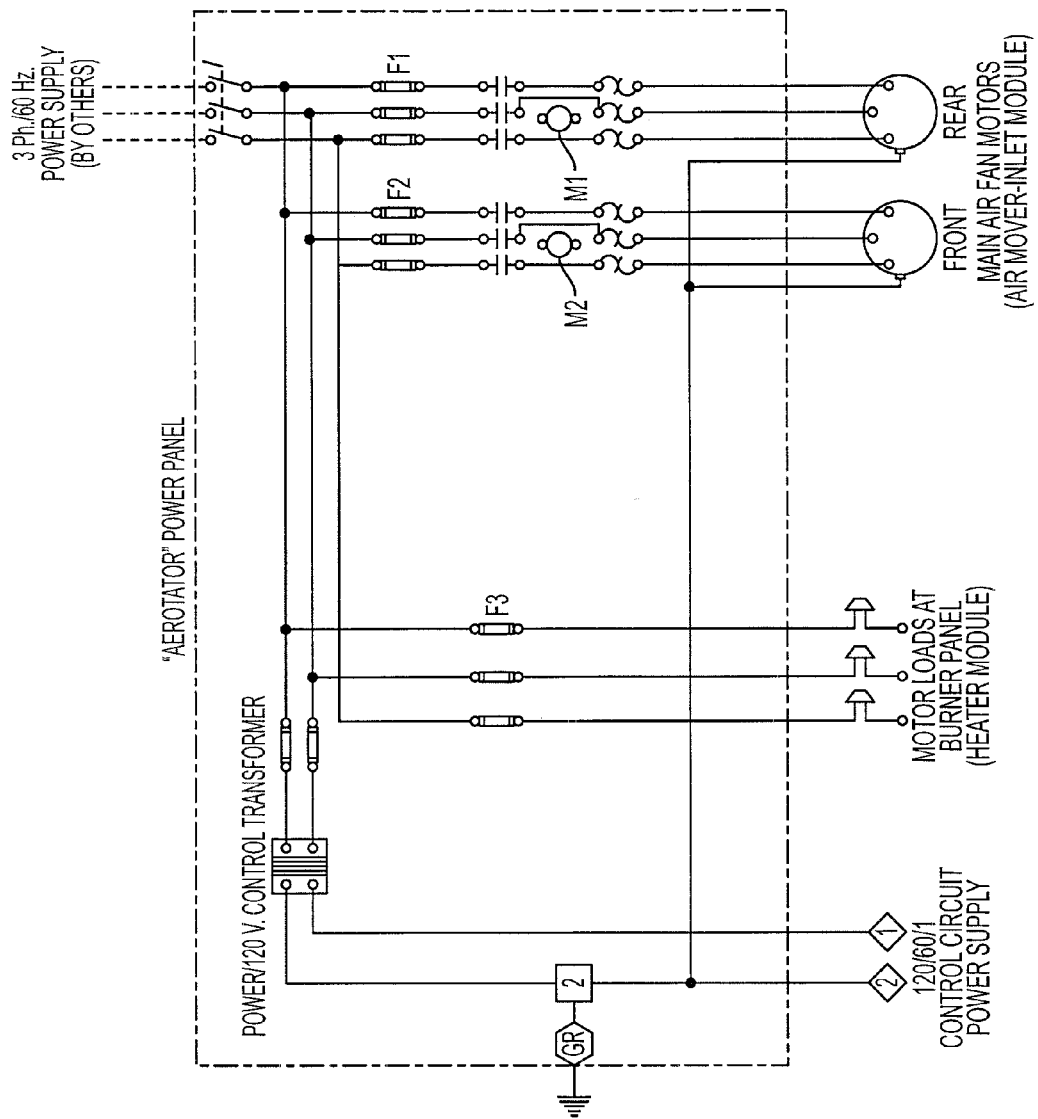
FIG. 14 is another circuit diagram of an embodiment of an air handling and conditioning system.

FIGS. 13 and 14 provide embodiments of circuit diagrams associated with the air handling and conditioning system (601). FIG. 13 shows an embodiment of control over the heating system, while FIG. 14 shows an embodiment of control over the power running the air handling and conditioning system.

With reference to the air handling and conditioning system for the hydroponic production of photosynthetic organisms: this system may incorporate an air conditioning package capable of operation with seasonal outside temperature variations from −40 degrees Fahrenheit to at least +100 degrees Fahrenheit. The fresh air intake through the intake is generally a minimum of 10% of the system total air supply quantity at all times during the year. The outside air compensates the system on a year-round basis and maximum economy is achieved by using more than minimum outdoor air for atmospheric cooling when outside conditions permit, i.e., during marginal or in-between seasonal conditions allowing for consideration for maximizing algae growth. When the air handling and conditioning system (601) is energized, a supply fan and exhaust fan start operating. A changeover thermostat selects either the summer or winter compensation mode according to outdoor temperature. At no-load condition, this schedule will change over automatically.

On the winter compensation schedule, an electronic control panel controls the space temperature by coordinating signals from the internal space thermostat discharge thermostat and an outdoor thermostat. An electric heating coil is also preferably provided with a step controller (not shown) whereby to sequence the electric heating coils depending on air temperature requirements. Outdoor and return air louvers may also controlled. The cooling coils are controlled by a valve, depending on space temperature requirements.

It is pointed out that an outside air thermostat may be adjustable either to overcome system offset or elevate the space temperature within the enclosure as the outside temperature falls. The electronic control panel may program signals from the humidistat to control humidification levels in the space.

In the summer compensation mode, the electronic panel controls the space temperature by coordinating signals from the space thermostat and outdoor thermostat to operate the cooling valve and cooling coil bypass dampers for cooling the outdoor and return air, for ventilating, or electric heating element sequencing for heating depending on interior space temperature. The outdoor air thermostat causes the space temperature to elevate as the outside air temperature rises. When the outside air is too warm, the outside air thermostat will return the outdoor air damper to its minimum position (as established by a minimum position switch) to eliminate outside excess flesh air and provide economical operation of the refrigeration equipment.

Under normal operation, the outdoor air damper motor positions the dampers at their minimum position except when outside air is used for atmospheric cooling. A thermostat provides signals concerning the return air temperature in the mixing box section. The motor controls the dampers and these dampers are adjusted so that they do not completely close thereby preventing the cooling coils from frosting the dampers. As herein shown, the exhaust air is also controlled by dampers, which are controlled by a motor, which connects to the electronic control panel. Although not shown, the electronic control panel is preferably a fully automated, computer-controlled panel and, with its sensor system, is capable of operating the air conditioning system fully automatically. The electronic control panel can also be integrated in a central processing unit (CPU) as understood by those of ordinary skill in the art whereby all working aspects of the hydroponic growing system are fully integrated. The CPU can also provide for system monitoring and adjustments through a computer located elsewhere.

In another embodiment, the air handling system (601) is a central system supplying pressurized air exiting said air outlet, and a return air outlet for conditioning and recalculating said return air.

As discussed above, in an embodiment, there is also provided a water holding tank capable of supplying temperature-adjusted water directly to the header pipe for irrigation of the cradles (401) if needed. The water tank is preferably designed for loading through bottom inlets. The tanks are also designed for easy washdown and bottom draining. The air conditioning delivers a constant air flow substantially evenly across each layer of the multi-layered growing cradles positioned in the racking system to provide carbon dioxide and temperature control. Carbon dioxide may be provided as simply part of temperature controlled air or may be supplied at an increased rate, as desired. In an embodiment, waste carbon dioxide is piped into the air handling unit to be supplied.

The hydroponic growing enclosure (100) and method of the present invention generally serves to produce an abundance of photosynthetic organisms, particularly algaes, which are generally free from impurities. Further, the various apparatuses and process used are generally designed for low maintenance and minimum operational manpower while also growing the algae in controlled conditions. Further, in an embodiment, the enclosure and method can provide for algae, which is commercially valuable, from various waste products including carbon dioxide from industrial process, sewerage and liquefied animal waste.

In an embodiment, the structure (101) and related components are designed for simple set up and tear down, being generally modular and providing for a simple connection of structural and operating equipment modules. The system can be field-serviced by on-site personnel for routine items or transported, in a trailer, for relocation or major repair. This allows for seasonal consumption or growing based on various demand factors. Further, as algae can generally be grown in only a few days, demand spikes for algae products can be fairly quickly compensated for by simply increasing algae output if additional capacity is available.

The enclosure and related structures are generally set up to operate from standard power lines depending on site conditions. In a preferred embodiment, the enclosure and process operates on a 220/110 volt service with back-up diesel generation on site. The main control panel located in the control room houses a set programmed chip which uses a sensor network to relay information to modular programmable controls located in the unit. These controllers can manually override any of the operating systems or be reset to auto pilot. The main control panel is equipped with communication ports for site and remote data downloading. The structure (101) may also be networked with other similar structures to allow making the enclosure (100) to operate together.

While the invention has been disclosed in conjunction with a description of certain embodiments, including those that are currently believed to be the preferred embodiments, the detailed description is intended to be illustrative and should not be understood to limit the scope of the present disclosure. As would be understood by one of ordinary skill in the art, embodiments other than those described in detail herein are encompassed by the present invention. Modifications and variations of the described embodiments may be made without departing from the spirit and scope of the invention.

The invention claimed is:

1. A system for hydroponically growing photosynthetic microorganisms comprising:
    a structure comprising a skeleton, a translucent membrane placed over said skeleton in a manner designed to be permanent, and a grid system affixed to said skeleton;
    a control compartment, further comprising a plurality of storage tanks and controls for said system, wherein at least a first storage tank of said plurality of storage tanks contains a liquid medium, at least a second storage tank of said plurality of storage tanks contains microorganisms, and at least a third storage tank of said plurality of storage tanks acting as a mixing tank within which said liquid medium is mixed with said microorganisms in predetermined quantities to form a slurry;
    a plurality of open cradles placed generally horizontally within said structure and capable of receiving said slurry through an inlet end, and permitting harvest of said microorganisms through an outlet harvest end; wherein said plurality is vertically racked; and wherein each of said cradles in said plurality has a downward slope to permit said slurry to move from said inlet end to said outlet harvest end in a manner that permits growth of said microorganisms;
        a handling system capable of conveying predetermined quantities of material stored within said storage tanks to at least one cradle of said plurality of cradles; and
        an air handling and conditioning system providing climate control within said structure, and maintaining the integrity of said structure.

2. The system of claim 1 wherein said air handling and conditioning system includes a mechanical operating system, comprising a fan, a heater, and a cooling element.

3. The system of claim 1 further comprising means for distributing carbon dioxide to at least one of said plurality of cradles.

4. The system of claim 1 wherein said air handling and conditioning system makes available a continuous conditioned and filtered air flow across all of said cradles.

5. The system of claim 1 further comprising a light source capable of radiating light from under said cradles to said microorganisms.

6. The system of claim 5 wherein said light source comprises a tube structure enclosing a plurality of light bulbs and affixed on said cradles' underside, and wherein said underside is translucent or transparent.

7. The system of claim 1 wherein said microorganisms are algae.

8. The system of claim 1 wherein said microorganisms are bacteria.

9. The system of claim 1 wherein said liquid medium comprises substances derived from farming excess, and water.

10. The system of claim 1 wherein said translucent membrane is an outer membrane, and said structure further comprises an inner membrane.

11. The system of claim 1 further comprising means for harvesting by froth floating, flocculating, dissolved air floating, or centrifuging.

12. The system of claim 11 further comprising means for processing by centrifuging or homogenizing.

13. The system of claim 12 wherein said controls automate said mixing of said slurry, said receipt of said slurry, said movement of said slurry, operation of said handling system, operation of said means for harvesting, and operation of said means for processing.

14. A method of hydroponically growing photosynthetic microorganisms comprising:
    having a self-contained growing enclosure, comprising an air supported structure further comprising a translucent membrane;
    installing a racking system, comprising a plurality of racked, generally horizontal, open cradles, within said enclosure, said cradles having a downward slope of 5 degrees or less;
    controlling temperature within said enclosure;
    mixing a predetermined quantity of liquid medium from a first storage means with a predetermined quantity of said microorganisms from a second storage means to form a slurry;
    placing said slurry in a predetermined number of said cradles at an inlet end of said cradles;
    distributing carbon dioxide to said cradles;
    causing said slurry to flow from said inlet end to an outlet harvest end of said cradles in a manner that permits multiplication of said microorganisms;
    making available a continuous conditioned and filtered air flow across all of said cradles;
    harvesting said microorganisms at said outlet harvest end; and
    processing said microorganisms to obtain molecules useful in fuel, wherein said microorganisms are separated into oil and solids.

15. The method of claim 14 further comprising a step of radiating light from under said cradles to said microorganisms.

16. The method of claim 14 wherein said microorganisms are algae.

17. The method of claim 14 wherein said microorganisms are bacteria.

18. The method of claim 14 wherein said step of placing is aided by gravity.

19. The method of claim 14 wherein said step of causing is aided by gravity.

20. The method of claim 14 wherein said carbon dioxide is drawn from a storage means.

21. The method of claim 14 wherein said step of making is performed by an air handling and conditioning system.

22. The method of claim 14 wherein said liquid medium comprises substances derived from farming excess and water.

23. The method of claim 14 wherein said membrane is an outer membrane, and said structure further comprises an inner membrane, a skeleton, a grid system affixed to said skeleton, a fan, a heater, and a cooling element.

24. The method of claim 14 wherein said step of distributing is performed by a perforated tube present along said cradles' length.

25. The method of claim 14 wherein said step of harvesting comprises froth floating, flocculating, dissolved air floating, or centrifuging.

26. The method of claim 14 wherein said step of processing comprises centrifuging or homogenizing.

27. The method of claim 14 wherein said steps of mixing, placing, distributing, causing, making, harvesting, and processing are continuously repeated.

28. The method of claim 14 wherein said steps of mixing, placing, distributing, causing, making, harvesting, and processing are automatically controlled.

29. A method of providing beneficial by-products of photosynthetic microorganisms, the method comprising:
deriving a liquid medium;
storing said liquid medium in a first storage means;
storing microorganisms in a second storage means;
mixing a predetermined quantity of said liquid medium from said first storage means with a predetermined quantity of said microorganisms from said second storage means to form a slurry, wherein said slurry is stored in a third storage means that is in fluid communication with said first storage means and said second storage means;
storing carbon dioxide in a fourth storage means;
having a self-contained growing enclosure, comprising a structure further comprising a translucent membrane;
installing a racking system, comprising a plurality of racked, generally horizontal, open cradles, within said enclosure, wherein said racking system is in fluid communication with said third storage means, and said fourth storage means;
controlling temperature within said enclosure;
placing said slurry in a predetermined number of said cradles at an inlet end of said cradles;
distributing a predetermined quantity of said carbon dioxide from said fourth storage means into said cradles via said fluid communication;
causing said slurry to flow from said inlet end to an outlet harvest end of said cradles in a manner that permits multiplication of said microorganisms;
making available a continuous conditioned and filtered air flow across all of said cradles;
conveying said microorganisms from said outlet harvest end to a means for harvesting;
harvesting said microorganisms with said means for harvesting;
processing said microorganisms by separating said microorganisms into oil and solids; and
distributing by products of said microorganisms.

30. The method of claim 29 wherein said step of harvesting comprises froth floating, flocculating, dissolved air floating, or centrifuging.

31. The method of claim 29 wherein said step of processing comprises centrifuging or homogenizing.

32. The method of claim 29 further comprising a step of radiating light from under said cradles to said microorganisms.

33. The method of claim 29 wherein said microorganisms are algae.

34. The method of claim 29 wherein said liquid medium comprises substances derived from farming excess and water.

35. The method of claim 29 wherein said steps of mixing, placing, distributing, causing, making, harvesting, and processing are continuously repeated.

36. The method of claim 29 wherein said steps of mixing, placing, distributing, causing, making, harvesting, and processing are automatically controlled.

37. The method of claim 29 wherein said steps of mixing, placing, distributing, causing making, harvesting, and processing are performed at co-located facilities.

38. The method of claim 29 wherein said structure is supported by airbeams.

39. The method of claim 29 wherein said structure is tension-supported.

40. The system of claim 1 wherein each of said cradles has a downward slope between about 1 and about 5 degrees.

41. The system of claim 1 wherein each of said cradles has a downward slope of about 2 degrees.

42. The method of claim 29 wherein each of said cradles has a downward slope of between about 1 and about 5 degrees.

* * * * *